(12) United States Patent
Mann

(10) Patent No.: US 7,049,814 B2
(45) Date of Patent: May 23, 2006

(54) NUCLEAR QUADRUPOLE RESONANCE BASED INSPECTION SYSTEM USING A HIGHLY RESONANT AND COMPACT MAGNETIC STRUCTURE

(75) Inventor: Kenneth Robert Mann, Surrey (GB)

(73) Assignee: Rapiscan, Inc., Hawthorne, CA (US)

( * ) Notice: Subject to any disclaimer, the term of this patent is extended or adjusted under 35 U.S.C. 154(b) by 121 days.

(21) Appl. No.: 10/751,563

(22) Filed: Jan. 5, 2004

(65) Prior Publication Data

US 2005/0146333 A1      Jul. 7, 2005

(51) Int. Cl.
*G01V 3/00* (2006.01)

(52) U.S. Cl. ...................... 324/300; 324/307

(58) Field of Classification Search ............. 324/300, 324/319, 322, 309, 307, 311; 600/410
See application file for complete search history.

(56) References Cited

U.S. PATENT DOCUMENTS

| | | | | |
|---|---|---|---|---|
| 3,427,532 | A * | 2/1969 | Nelson | 324/308 |
| 5,233,300 | A * | 8/1993 | Buess et al. | 324/307 |
| 5,457,385 | A * | 10/1995 | Sydney et al. | 324/301 |
| 5,592,083 | A * | 1/1997 | Magnuson et al. | 324/300 |
| 6,194,898 | B1 * | 2/2001 | Magnuson et al. | 324/300 |
| 6,291,994 | B1 * | 9/2001 | Kim et al. | 324/300 |

FOREIGN PATENT DOCUMENTS

EP          1253433 A1 * 12/1899

* cited by examiner

Primary Examiner—Brij B. Shrivastav
(74) *Attorney, Agent, or Firm*—PatentMetrix

(57) ABSTRACT

The present invention is directed toward a magnetic resonance based material detection system that includes a resonator probe which is highly resonant, is cost effective and has a compact magnetic structure with a low cost tuning mechanism and high quality factor (Q). The probe is relatively immune to radio frequency interference and can be used in close proximity to other resonator probes of similar design, complementary sensing equipment, and electromagnetic shielding due to its low external magnetic field. It is preferred that, if the magnetic resonance based detection equipment is used with complementary sensing equipment that uses x-rays, the portion of shielding that intersects the x-ray beam is made of thin material of a conductive nature which retains electromagnetic shielding properties while causing minimal attenuation to x-rays. In one embodiment, the resonator probe is a rectangular-shaped single turn toroid fabricated from copper sheets. The resonator probe also has adjacent walls forming an inspection volume such that materials can be passed through this inspection volume.

19 Claims, 8 Drawing Sheets

FRONT VIEW

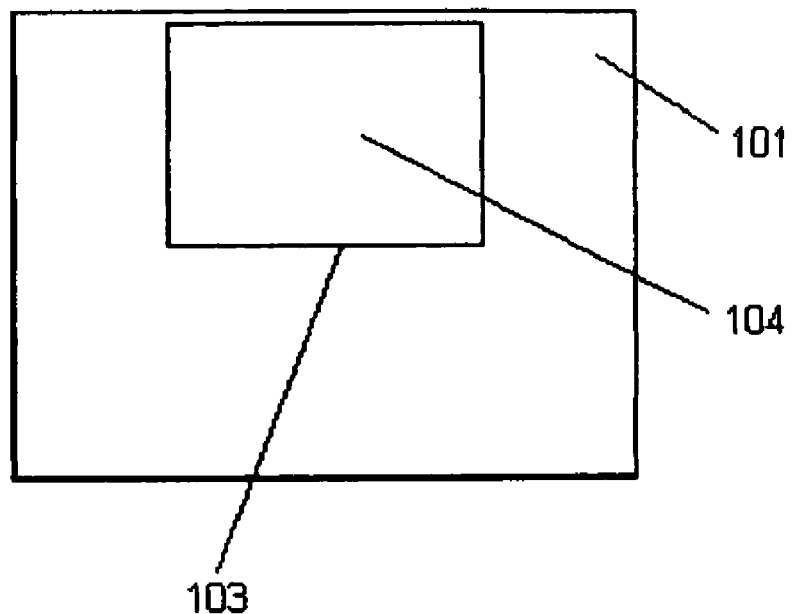
Fig 1(a) FRONT VIEW
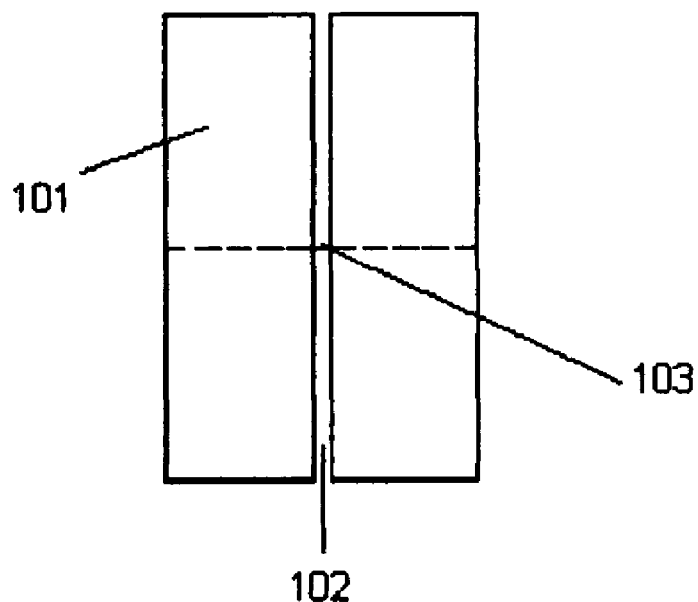
Fig 1(b) SIDE VIEW

Fig 1(c) TOP VIEW

NUCLEAR QUADRUPOLE RESONANCE BASED INSPECTION SYSTEM USING A HIGHLY RESONANT AND COMPACT MAGNETIC STRUCTURE

FIELD OF THE INVENTION

The present invention relates generally to a magnetic resonance based material detection and/or analysis system and more particularly to Nuclear Quadrupole Resonance (NQR) based material detection and/or analysis system based around a compact, interference immune and highly resonant probe design. In addition the present invention employs a cost effective tuning mechanism that can be used in close proximity to other resonator probes of similar design, complementary sensing equipment, and electromagnetic shielding. Further, the invention relates to the use of two or more similar resonator probes, operated in conjunction with a single tuning mechanism.

BACKGROUND OF THE INVENTION

NQR is a magnetic resonance technique, closely related to Nuclear Magnetic Resonance (NMR), suitable for detection and/or analysis of bulk materials that contain a quadrupolar nucleus. Examples of such materials are nitrogen-containing explosives such as RDX, TNT and PETN and chlorine-containing narcotics such as heroin and cocaine. An advantage of NQR over NMR is that there is no requirement for a strong direct current (DC) magnetic field. This removes the need for a large, expensive, typically super conducting, electro-magnet.

Atomic nuclei with a spin quantum number of greater than ½ and having non-spherical electric charge distributions possess electric quadrupole moments. Quadrupole resonance arises from the interaction of the nuclear quadrupole moment of the nucleus with the local applied electric field gradients produced by the surrounding atomic environment.

NQR analysis for a given material involves the irradiation of a sample that has been placed in a test volume with a pulsed RF magnetic field. The frequency of the applied field used must be at or very close to one of the nuclear quadrupole resonance lines of the material under analysis. These frequencies are unique to individual materials and therefore allow for very specific identification of a material under analysis.

NQR has applications in a number of fields including security screening for the detection of drugs or explosives in bags, cargo etc.; landmine detection; pharmaceutical processing; pharmaceutical and chemical production quality control; and strain gauge measurements.

In the past, baggage screening systems have employed NQR to identify suspect bags that may contain contraband. U.S. Pat. Nos. 5,206,592 and 5,233,300 describe methods and systems for detecting nitrogenous explosives and narcotics employing NQR techniques. These techniques, however, have lower signal to noise ratio causing problems due to interference from external signals, thereby masking the signal.

Typically these systems will sequentially search for two or more explosive materials using pulse sequences at multiple frequencies corresponding to the NQR frequencies of the materials being searched. A high frequency resonant circuit is used to generate the magnetic field required to excite the NQR signal and subsequently to detect the generated magnetic response. These systems are built with a high quality factor (Q), which is important for two reasons. Firstly, the signal to noise ratio of any signal detected is directly related to $Q^{1/2}$. Secondly, the power required to generate a suitable excitation signal is directly related to the Q factor.

Essentially, resonator probes previously used in this manner have been single turn solenoids made from sheet copper with a gap in them, which are bridged with capacitors. The capacitors are selected such that the resonant frequency of the coil/capacitor combination is the same as the NQR frequency of the material under investigation.

There are several limitations inherent to solenoidal coil design. Solenoidal coils are good magnetic structures for generating homogeneous RF magnetic fields. However, half of the magnetic flux generated by such a structure is outside the structure. Owing to the nature of magnetic fields, unless this external flux is constrained by a shield, it will be measurable at considerable distances from the solenoid. Although the addition of electromagnetic shielding considerably reduces this, inadequate shielding leads to two primary problems. Firstly, magnetic fields generated within the system escape at sufficient levels such that the fields generated interfere with other electrical equipment. Secondly, electromagnetic interference generated outside the equipment can be picked up by the equipment and can interfere with the highly sensitive NQR measurement.

To allow for effective performance of the probe coil, the shield must be suitably spaced from the resonator probe. Additional magnetic probes within the same shield must be at considerable distances from the first probe and each other. In effect, this means that it is generally practical to put only one resonator probe in a shield. The shield used must also be significantly larger than the resonator probe it is shielding.

U.S. Pat. Nos. 5,592,083, 6,194,898 and 6,291,994 disclose a NQR based contraband detection system with electromagnetic shielding to mitigate low signal to noise ratio and the presence of external interference signals. In these systems, the RF coil is comprised of a hollow rectangular tube of thin sheet conductive material formed on a thin-walled rectangular insulator. The shield is a rectangular conductor sleeve, comprised of a copper or any other highly conductive material, and encloses the probe coil. U.S. Pat. No. 6,522,135 discloses a rectangular resonator probe employed to detect NQR in the sample.

Such systems will have a single inspection resonator probe that scans at the frequency corresponding to the first target material. If it is necessary to investigate a second material the resonator probe is then retuned by switching its resonant frequency to that of the second target material. The frequency of operation is typically changed by switching the amount of capacitance in and out using relays or mechanical actuators. In addition to this coarse frequency adjustment it may be necessary to fine tune for each frequency range depending on the electrical properties of the item (bags or packages) that is being examined. Conductive or high permeability, materials in particular, will alter the inductance of the resonator coil and, therefore, its tune frequency. The de-tuning effect of the bag on the resonator probe will differ from bag to bag depending on their contents and construction. As a result the probe must be retuned to a new NQR frequency. U.S. Pat. No. 5,457,385 discloses a NQR based detection system having an array of excitation devices (RF coils) tuned at different frequencies for determining the presence of selected nuclei in an article. These systems, however, require costly tuning relays for tuning the system to one or more requisite NQR frequencies.

Since much of the equipment that uses this technology is for use in airports, where space is at a premium, it is desirable to build systems as compactly as possible. Furthermore, this technology complements existing airport screening equipment, for example X-ray machines and Computed Tomography (CT) machines. U.S. Pat. Nos. 5,168,224 and 5,642,393 disclose an inspection system for detecting a specific substance in an article using an X-ray inspection apparatus in conjunction with NQR measurement equipment. The resulting solenoidal resonator probe design, however, does not lend itself to close integration with parts of other existing sensor systems.

At present, solenoidal resonator probes have been used because it is practical to use only one inspection resonator probe even when systems are investigating for the presence of more than one material at more than one frequency. As described above, this is achieved by using either relays or mechanical actuators to switch between varying capacitance values. This is disadvantageous because the relays and mechanical actuators used must have very low contact resistance to minimize the resistive losses within the resonant circuit and therefore maximize the Q-factor. Even the use of high quality components is not completely effective in countering resistive loss. Typically, the lower frequency ranges suffer the most from additional loss because the lower the frequency the more additional capacitance that has to be switched in. Additionally, it is often the lower frequencies that have lowest NQR sensitivity due to the lower induced signal voltages picked up at lower frequency.

Another disadvantage in switching the resonant frequency of a single resonator probe is that the relays or mechanical actuators described above are very expensive. Typically, they are one of the most expensive components of the resonator probe. Additionally, since relays and actuators are predominantly mechanical devices they are also one of the most likely components within the resonator probe to suffer from mechanical failure. Often multiple relays are connected in parallel to yield the desired low contact resistance. It becomes difficult to diagnose the problem if any one of these devices fails.

European Patent Application No. 1,253,433 discloses an extended toroidal design for the resonator probe. The resonator probe is designed to improve sensitivity to signals generated within a sample volume while improving insensitivity to background noise. It also discloses a tuning vane provided within the hollow central portion of the resonator probe for varying inductance of the probe coil for the purpose of tuning. This design does not, however, lend to efficient integration of additional resonator probes or other existing screening systems.

Thus, what is needed is a compact resonator probe that can be placed in proximity to shielding devices, additional resonators probes, and other components of an article screening system. What is also needed is a resonator probe in which the number of relays or mechanical actuators employed is reduced or eliminated.

SUMMARY OF THE INVENTION

In one embodiment, the present invention is directed toward a resonator probe suitable for use in a magnetic resonance based material detection system. The resonator probe comprises a hollow resonator probe body made from an electrically conductive material wherein the probe body has a rectangular volume and at least one resonant frequency, an inspection volume integrally formed within the hollow resonator probe body, the inspection volume defined by a platform base, an inner top wall, and two inner side walls, the inner side walls connecting the top inner wall and platform base, wherein a sample of material passes through the inspection volume; and a capacitance means electrically connected to the hollow resonator probe body.

Optionally, the resonator probe body is an elongated, square sided toroid. The capacitance means is provided in the resonator probe body, distributed around a split in the body, is adjustable (by allowing the resonant frequency of the resonator probe to be adjusted), and/or runs parallel to a magnetic flux path generated within the resonator probe body. Optionally, the rectangular volume is an inductive portion of a resonant circuit.

In another embodiment, the resonant frequency of the resonator probe is determined by an inductance of the resonator probe and a capacitance of the capacitance means. The inductance of the resonator probe is adjustable by providing a means to adjust a cross-sectional area of said resonator probe body. Optionally, the means to adjust the cross-sectional area of the probe body is comprised of a tuning vane.

In another embodiment, the resonator probe further comprises an outer electrically conductive electromagnetic shielding layer surrounding the resonator probe body having an opening aligned with said inspection volume. The shielding layer may have thinned areas of conductive material such that electromagnetic shielding is maintained while, in the thinned areas, x-rays can pass with minimal attenuation.

In another embodiment, the present invention is directed toward a system for adjusting an inductance of a plurality of resonator probes comprising a means for binding the motion of a plurality of tuning vanes wherein each tuning vane adjusts a cross-sectional area of a segment of respective resonator probes and a means to drive the binding means. Optionally, the binding means is a plurality of belts and the driving means is a servomotor.

In another embodiment, the present invention is directed toward a magnetic resonance based material detection and/or analysis system comprising a plurality of resonator probe bodies, wherein the plurality of resonator probe bodies comprise a hollow resonator probe body made from an electrically conductive material wherein the probe body has a rectangular volume and at least one resonant frequency, an inspection volume integrally formed within the hollow resonator probe body, the inspection volume defined by a platform base, an inner top wall, and two inner side walls, the inner side walls connecting the top inner wall and platform base, wherein a sample of material passes through the inspection volume, and capacitance means electrically connected to said hollow resonator probe body; a radio frequency pulse generator connected to the probe for producing an applied magnetic field within at least one probe body; a sensor for detecting a magnetic field produced by a sample after being exposed to the applied magnetic field; and a controller to selectively energize the radio frequency pulse generator and/or sensor.

In another embodiment, the present invention is directed toward a method for performing magnetic resonance based material detection and/or analysis comprising the steps of activating a radio frequency pulse generator to produce an applied magnetic field within at least one probe body; and sensing a magnetic field produced by a sample after being exposed to said applied magnetic field; wherein the at least one probe body is hollow and made from an electrically conductive material; wherein the probe body has a rectangular volume; wherein an inspection volume is integrally formed within the hollow resonator probe body; and wherein a capacitance means is electrically connected to said hollow resonator probe body.

It is an object of the present invention to provide a novel highly resonant, low cost, and compact magnetic structure (resonator probe), having a high quality factor (Q) and a cost effective tuning mechanism, which can be employed in NQR analysis.

It is another object of the present invention to provide a novel design for the resonator probe that is relatively immune to external interference and effectively generates reduced interference when compared with previously used coil configurations.

Yet another object of the present invention is to provide a novel highly resonant magnetic structure that can be used in close proximity to electromagnetic shielding, other similar resonant structures, and/or complementary sensing/analysis equipment.

It is a further object of the present invention to provide a method of fine-tuning two or more novel highly resonant structures simultaneously.

It is a still further object of the present invention to provide a novel highly resonant structure that can achieve the same performance as previously used coil configurations without such demanding levels of electromagnetic shielding.

It is a still further object of the present invention to provide a method of electromagnetically shielding the highly resonant structure or structures that allows x-rays to pass though it with minimal attenuation.

It is a still further object of the present invention to provide a screening or analysis system that employs two or more novel highly resonant structures to achieve multiple frequency ranges with a reduced need for switching components.

The novel highly resonant and compact magnetic structure (resonator probe) is made preferably from a flat sheet of copper (or other comparable conductive material, such as silver, aluminum, or any other material) shaped to form an elongated, square sided toroid. The more fully enclosed resonator design disclosed herein has further improved sensitivity to signals generated within the sample volume and offers further improved insensitivity to background noise.

BRIEF DESCRIPTION OF THE DRAWINGS

The objects, advantages and features of this invention will become apparent, but are not limited to, the detailed description, when read in conjunction with the accompanying drawings.

FIGS. 1(a), 1(b) and 1(c) are projection drawings depicting the resonator body showing the front view, side view and top view of the resonator body, respectively;

DETAILED DESCRIPTION OF THE DRAWINGS

The present invention relates to a Nuclear Quadrupole Resonance (NQR) based material detection and/or analysis system. The NQR system of the present invention employs a vane-tuned enclosed resonator coil design which is more compact, less susceptible to receive or generate radio frequency interference, has a low manufacturing cost, has reduced flux leakage and can be placed close to other resonator probes of similar design and sensing equipments.

Figure 1D:
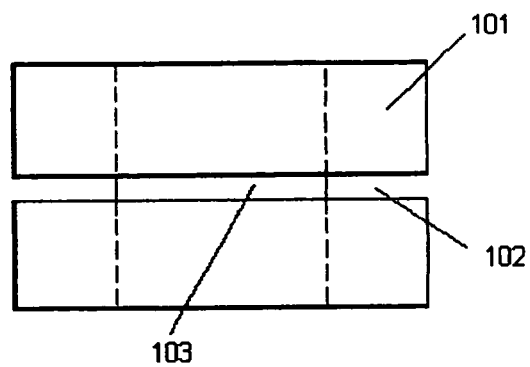
FIG. 1(d) depicts a perspective view of the resonator body.
Figure 1D:
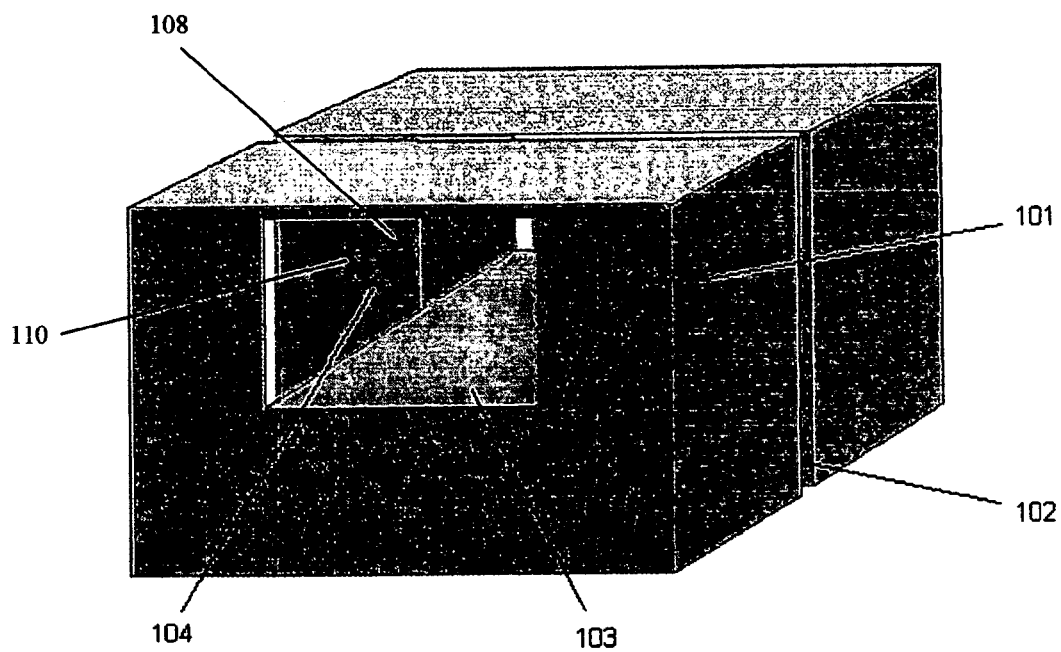

FIG. 1(a), 1(b), 1(c) and 1(d) show the front view, side view, top view, and isometric or perspective view of the resonator probe body, respectively. Referring to FIG. 1(a), the probe or basic resonator has a rectangular or cubic volume, referred to generally as a box-like structure 101, and is made from a conductive material. In one preferred embodiment of the invention, this conductive material is a metal due to its relatively low resistivity. More specifically the metal will be one of lower resistivity such as, but not limited to, silver, copper or aluminum. Copper is a preferred choice due to its high conductivity and relatively low cost. The box-like structure 101 is configured as an enclosed resonator probe, preferably with rectangular, orthogonal edges for manufacturing ease.

Referring to FIGS. 1(b) and 1(c), the box-like structure 101 has a continuous split 102 around the outside perimeter. The front side and back side of the box-like structure 101 are joined together, internally at the middle of the structure, by a platform 103 made from the same material as the box-like structure 101.

Referring to FIG. 1(d), the enclosed resonator probe 101 has platform 103, a top wall surface 108 parallel to platform 103, and two inner side walls 110, which connect the inner top wall surface 108 and platform 103, forming a rectangular cutout or inspection volume 104, through which samples to be analyzed are passed. It is preferred that the toroid of the present invention be rectangular and elongated rather than rounded and circular.

Figure 2A:
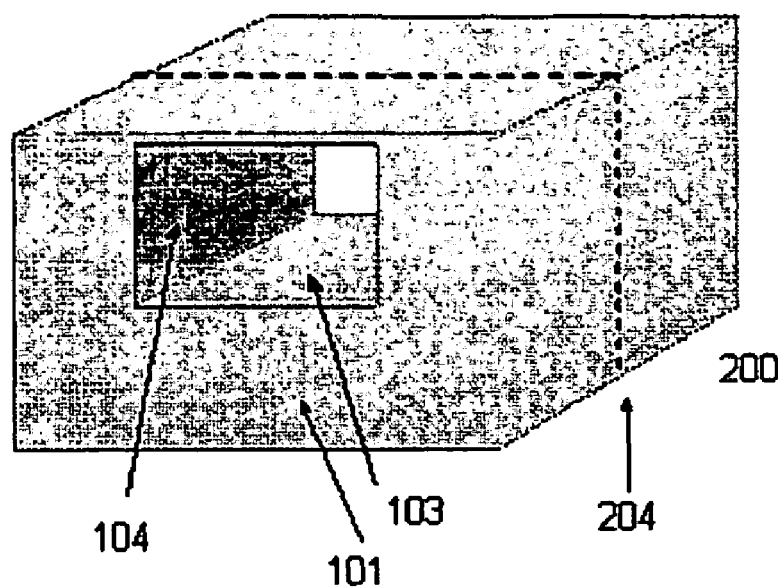
FIG. 2(a) illustrates the layout of an enclosed resonator probe showing the tuning capacitor.

FIG. 2(a) shows the layout of enclosed resonator probe 200. In one embodiment, enclosed resonator probe 200 is essentially a single turn toroid fabricated, in a preferred embodiment, from copper sheets. The toroid of the present invention is fabricated from flat sheets of copper bent and soldered into position, creating orthogonal sides, which reduce its manufacturing cost. The tuning capacitors 204 are provided in the probe body, distributed along the continuous split 102 around the perimeter of probe 200, and are electrically connected to the probe 200 to form either a series or parallel resonant LC circuit. The resonator probe 200 is therefore a highly resonant compact magnetic structure.

Figure 2B:
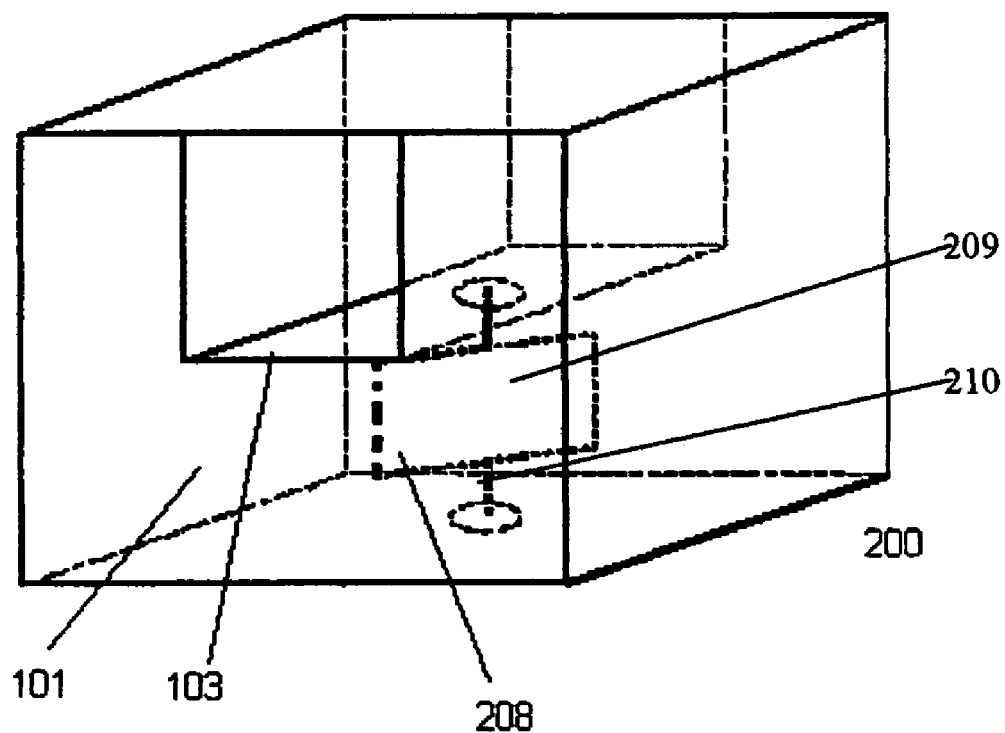
FIG. 2(b) is a drawing depicting the inspection volume or cutaway of the enclosed resonator probe showing a means of implementing a tuning vane.

FIG. 2(b) depicts the inspection volume 104 of the enclosed resonator probe 200 showing tuning vane 208 housed within the hollow central portion of enclosed resonator probe 200 and below platform 103. The tuning vane 208 comprises a conductive plate or loop 209 mounted on a pivot axle 210 passing through the enclosed resonator probe 200. The pivot axle may be rotated either manually or automatically via the control of a controller.

Figure 2C:
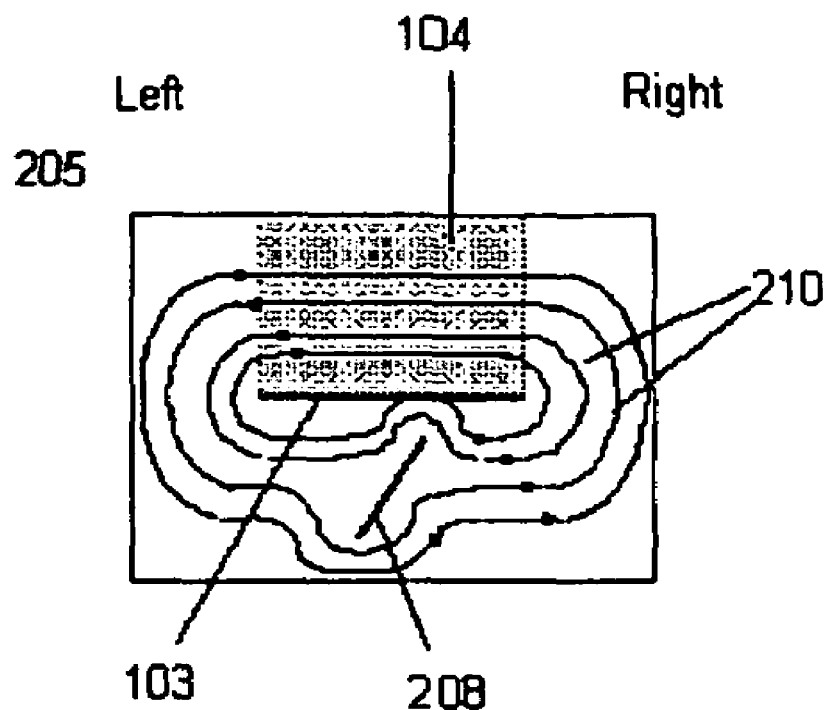
FIG. 2(c) is a drawing illustrating the coil cross-section and shows the magnetic flux path within the resonator body.

The box-like structure 101 provides the inductive component of a resonant circuit. It is the inductance of this box combined with the applied capacitance of tuning capacitors 204 that determines the resonant frequency of the enclosed resonator probe 200. Referring to FIG. 2(c), which depicts the enclosed resonator coil cross-section 205, the parallel currents that flow within the resonator probe 200 upon resonance pass from back to front across platform 103 in the center and radiate across the front face of resonator probe 200 outward from the platform 103 towards the outer perimeter (this path is distorted in the area of the hole in the front face). The currents then flow from the front to the back of resonator probe 200 across the outer walls of enclosed resonator probe 200, subsequently passing across the distributed capacitor 204. The currents pass from the outer perimeter on the back face of the resonator probe 200 towards the center of the back face to the platform 103.

This current path produces a magnetic flux path (or magnetic lines of force) 210 around the inside of the resonator probe 200 as shown in FIG. 2(c). The magnetic flux path 210 is parallel to and above the platform 103 across the inside of the inspection volume 104 within the enclosed resonator probe 200. It travels from left to right, and then turns around the end of the platform 103 and runs parallel and below the platform 103 from right to left. It then turns back upward at the right end of platform 103 and completes the loop. The tuning capacitors 204 distributed around the continuous split 102 in the resonator probe body 200 run parallel to the primary magnetic flux path 210.

The multiple parallel current paths resulting from the design of resonator probe 200 and distributed tuning capacitors 204 enables the resonator probe 200 to have a very low resistance, resulting in low resistive losses, and therefore a very high Quality (Q) factor. In addition, the design of the resonator probe 200 in the present invention leads to its low susceptibility to transmitting and receiving radio frequency interference or noise, and reduced flux leakage. The resonator probe 200 is an efficient magnetic structure with nearly all the magnetic flux generated by the system constrained within it, further allowing for a high Quality (Q) factor. A high Q factor is important in the effective performance of a resonator probe because the higher the resonator Q factor the higher the signal to noise ratio of any measurements made from test samples. A high Quality (Q) factor also leads to higher power efficiency.

Figure 2D:
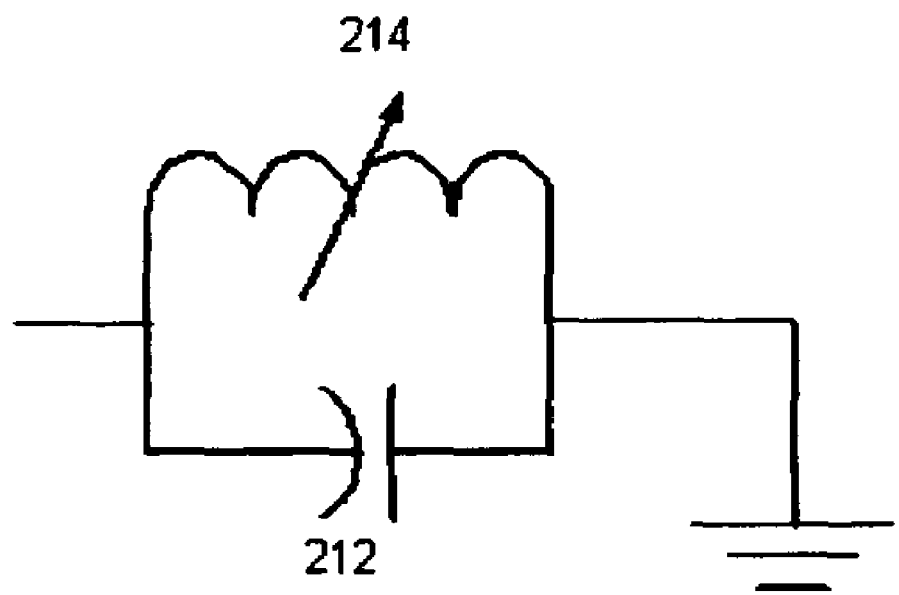
FIG. 2(d) depicts the equivalent circuit diagram of an enclosed resonator probe.

The equivalent circuit diagram of the enclosed resonator probe 200 is shown in FIG. 2(d). The resonant frequency of the enclosed resonator probe 200 is changed by either altering the inductance 214 of the resonator probe 200 or the applied capacitance 212 of the tuning capacitors 204, described above. In both cases this can be done either continuously or discreetly depending on which methods are chosen.

The applied capacitance 212 of the tuning capacitors 204 is adjustable by use of either variable capacitors or switches which add or subtract capacitance. A preferred method is to use a variable angle conductive vane 208 in the flux path within the resonator probe 200 as shown in FIGS. 2(b) and 2(c). Changing the angle of vane 208 effectively alters the cross-sectional area of a segment of the resonator probe 200, interrupting the flux path 210 within the resonator coil 200 to a variable degree. This has the effect of changing the resonator's inductance 214 and therefore, its resonant frequency. The closer the angle of the tuning vane 208 to normal (90 degrees) with respect to the flux path 210, the greater the area of flux path 210 intersected, the lower the inductance 214 and therefore the higher the resonator's 200 tuned frequency. The angle of tuning vane 208 can be changed in various directions provided that it is changing the amount of flux path 210 that is intersected. This method allows fine-tuning of the resonant frequency of the resonator probe 200. Alternatively, the inductance 214 can be adjusted by switching different sized conductive loops, which block different amounts of flux 210. Coarse adjustment of the resonant or tuning frequency of the resonator probe 200 is best achieved by switching the resonant circuit's tuning capacitance 212.

Figure 3A:
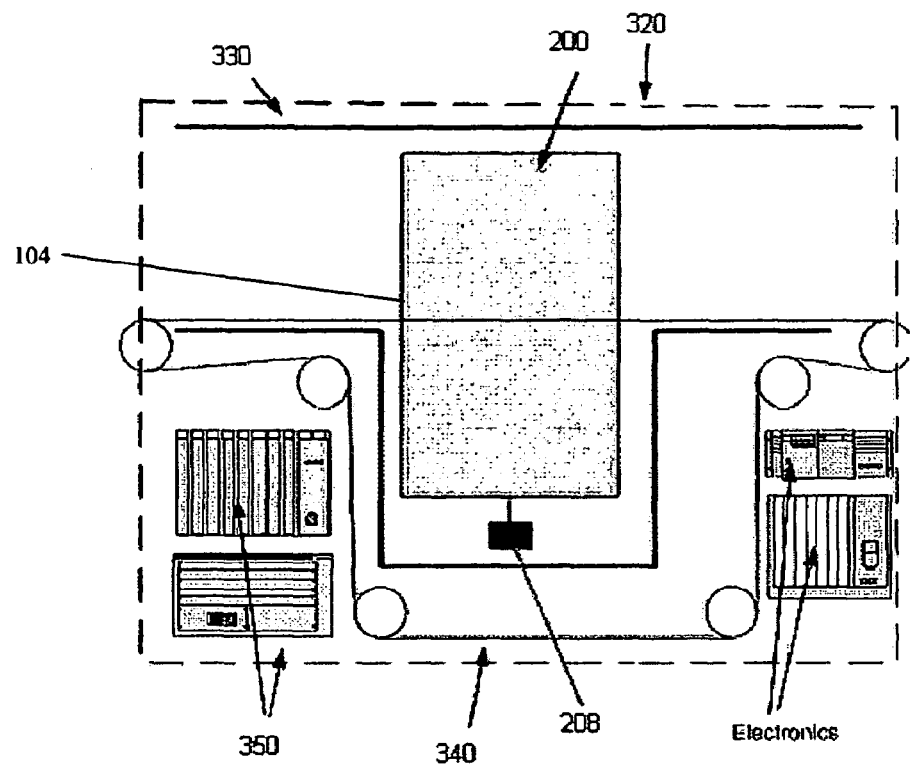
FIG. 3(a) is a drawing depicting the layout of a NQR baggage scanner having single resonator coil.

FIG. 3(a) illustrates the layout of an NQR baggage scanner employed to detect the presence of contraband within baggage. It is particularly effective in detecting contraband materials in configurations that are more difficult to detect using more established detection technologies since the result of an NQR scan of a material under analysis depends on the number of a specific quadrupolar nuclei present in the material, regardless of how those nuclei are distributed. The enclosed resonator probe 200 preferably made from copper is placed within an outer electrically conductive electromagnetic shield (or RF shield) 330, preferably made from, but not limited to aluminum. The electromagnetic shield 330 reduces the effect of external magnetic fields and also helps to constrain the generated magnetic and electric fields within the resonator probe 200. Thus the reliability of the analysis/detection is enhanced and resonator probe 200 remains essentially immune to external electromagnetic (RF) radiation. The electromagnetic shield 330 also protects the external electronic apparatus from picking up electromagnetic (RF) radiation generated by resonator probe 200. The resonator probe 200 is tuned at NQR frequencies of the target substance under detection or analysis. While the excitation frequency need not be exactly the same as the NQR frequency of the target substance, it is ideally within 500–1000 Hz. Tuning vane 208 is used for fine-tuning of the resonator probe 200.

A conveying means such as conveyor belt system 340 is provided through the inspection volume 104 in the resonator probe 200 for transporting the luggage through the inspection volume 104 of the scanner. The conveyor belt 340 may be continually or incrementally moved via the control of a controller to pass a series of samples through the resonator probe 200. The NQR scanner is preferably encased in its entirety in cosmetic outer panels 320. The necessary electronic circuits 350 are provided for generating RF pulses, measuring the NQR, detecting suspicious baggage, activating alarms, and tuning enclosed resonator probe 200.

Figure 3B:
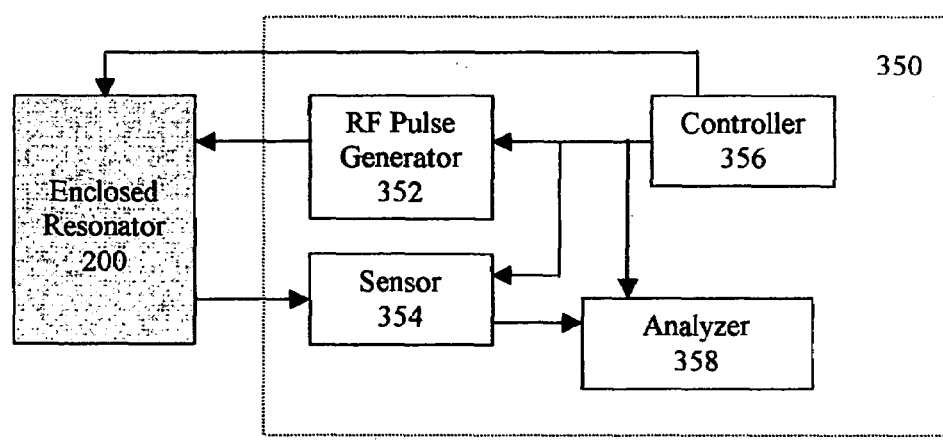
FIG. 3(b) is a diagram depicting the various elements of the electronic circuit needed to operate the baggage scanner shown in FIG. 3(a)

FIG. 3(b) diagrams various components of electronic circuit 350. Electronic circuit 350 comprises RF pulse generator 352, sensor 354, controller 356, and analyzer 358. RF pulse generator 352 provides electrical energy in the form of high power pulses to enclosed resonator probe 200. This electrical energy is converted into a magnetic field within resonator probe 200. In response to the applied magnetic field from resonator probe 200, the sample produces its own small magnetic field, which is then detected by sensor 354 and fed to analyzer 358. The controller 356 ensures that the RF pulse generator 352 and the sensor 354 are energized at the same time. Controller 356 controls the tuning of the resonator probe 200 by varying the angle of tuning vane 208 and also controls the conveyor belt system 340.

NQR is a form of linear spectroscopy; therefore, the signal strength is directly proportional to the detected quantity of contraband material containing quadrupolar nuclei. Because the NQR frequencies of different compounds are quite distinct, the system is less likely to encounter false alarms from the NQR signals of other materials, which may not be harmful. For example, $^{14}$N NQR absorption frequencies from crystalline materials are virtually unique. When looking for the nitrogen signal at the NQR frequency of RDX, for example, only nitrogen in RDX will be detected. If other compounds containing $^{14}$N are in the same parcel as the RDX, those other compounds would likely not be identified. The frequency resulting from NQR in a target substance will be sharply defined, while other $^{14}$N-containing substances would not provide a sharp peak NQR response.

In another preferred embodiment of the present invention, a plurality of resonator probes can be placed in proximity to each other within the same electromagnetic shield rather than using a single probe coil containing a number of expensive components for tuning to different frequencies for detecting various types of contraband. Each of the resonator probes, in this particular embodiment, is tuned to a different NQR frequency. In most cases, the fine-tuning for each unit is enabled via a single fine-tuning mechanism, responsible for controlling the plurality of resonator probes.

This arrangement has several advantages. It eliminates the need for costly tuning relays used for fine-tuning within a frequency range of a specific substance. In addition, this arrangement removes the need for costly bulk tuning relays or mechanical frequency switching actuators, used for coarse tuning. In this embodiment of the present invention, the Q factor remains high for all tuned frequencies since resonator coil currents are not affected by contact resistance resulting from tuning relays or actuators used to switch between frequency ranges. In addition, since no additional tuning is required for the second resonator coil, the scan time is reduced, thereby increasing the throughput of the screening system.

Figure 4:
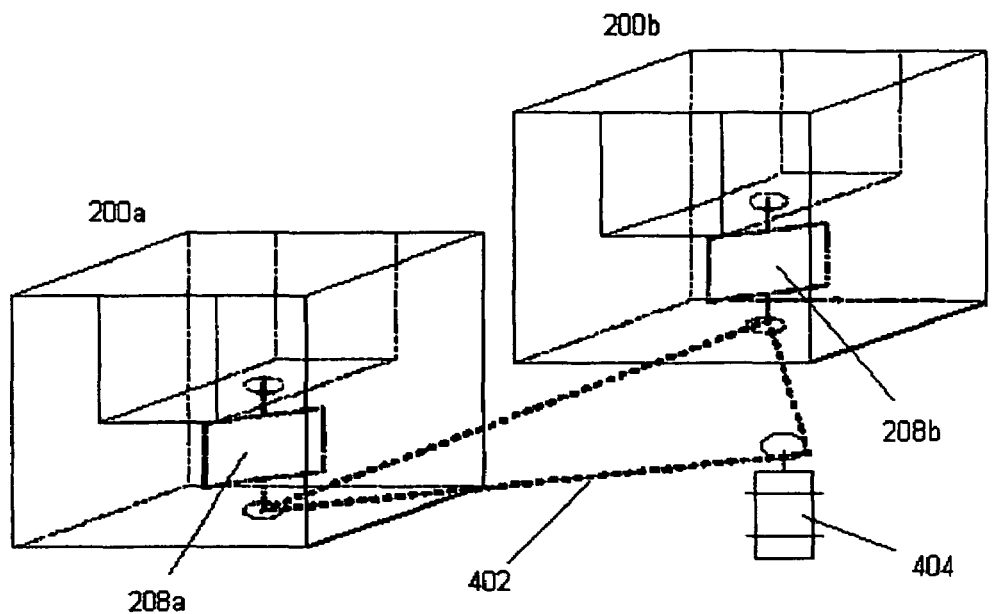
FIG. 4 is a diagram showing a single tuning mechanism for controlling tuning vanes of two or more resonator probes.
Figure 5:
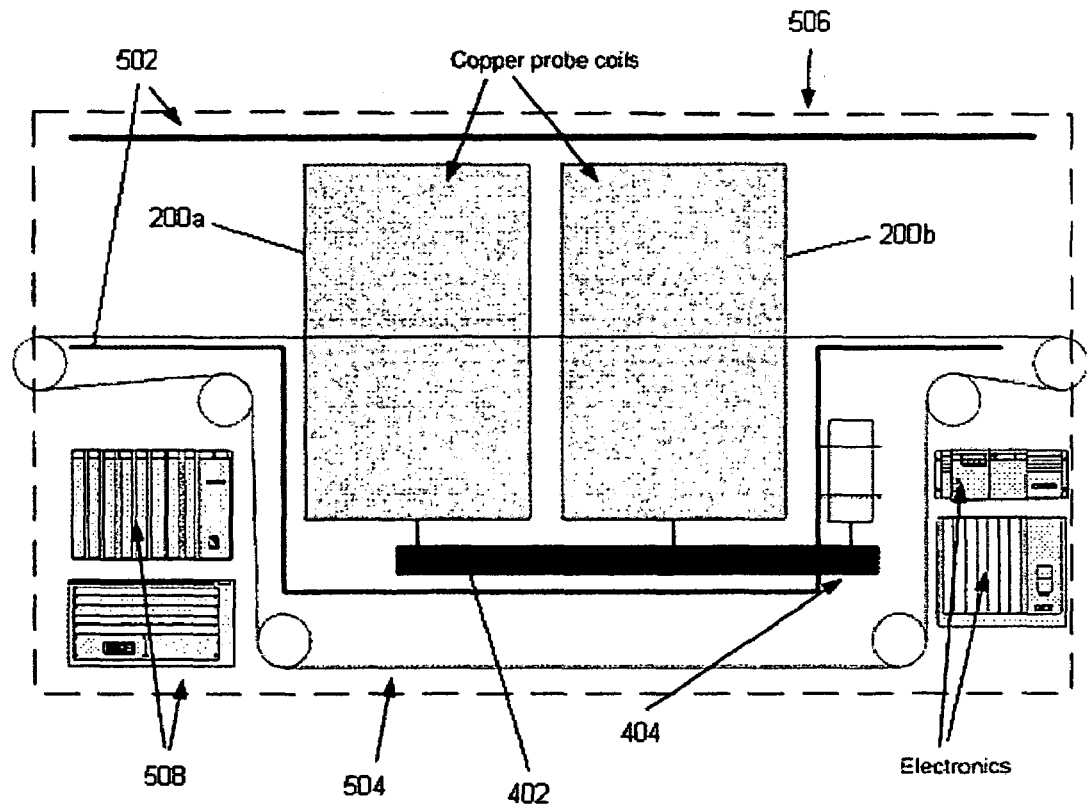
FIG. 5 is a diagram depicting the layout of a dual coil NQR baggage scanner with single tuning mechanism.

FIGS. 4 and 5 depict how the resonant frequency for more than one resonator probe can be driven from the same motor 404, which can in turn be driven from a single control system. This method of tuning multiple resonator probes can be extended from a minimum of two resonator probes to as many resonators probes as desired for a given system depending on the requirements for the system. A significant difference between this resonator probe configuration and other designs is the possibility of operating multiple resonator probes in close proximity with minimal mutual interference since most flux is constrained within the resonator coil itself.

FIG. 4 illustrates how, in one embodiment, two resonator probes 200a and 200b, employing this configuration can be used in conjunction with one another by tying together the motion of the individual vanes 208a and 208b, respectively, using belt 402. Additional belts 402 can be added to fine tune more resonator probes. A motor 404 is used to drive belt 402.

FIG. 5 illustrates the layout of a dual coil NQR baggage scanner used for detecting the presence of explosives and/or narcotic materials within closed or sealed packages or baggage. The two resonator probes 200a and 200b, preferably made of copper, are placed in proximity to one another within the same electromagnetic shield 502, preferably made of aluminum. The two probe coils 200a and 200b are tuned at different frequencies for detecting the existence of specified materials, such as RDX and PETN explosives for example. RDX-based plastic explosives have a resonant frequency of approximately 3.410 MHz while PETN-based plastic explosives have a resonant frequency of approximately 890 KHz.

The vane tuning servomotor system comprises motor 404 and belt 402, driving both tuning vanes 208a and 208b, and is used for fine-tuning the two resonator probes 200a and 200b. As described above, the conveyor belt system 504 and electronic circuit 508 are provided for transporting the luggage through the inspection volume 104, generating RF pulses, measuring the NQR, detecting suspicious baggage, activating alarms, and tuning the resonator probes 200a and 200b.

Also shown in FIG. 5 are two resonators probes, 200a and 200b, placed adjacent and in close proximity to one another forming a baggage screening system that does not need multiple switching devices to operate on two separate frequency ranges. Instead resonator probes 200a and 200b are used, one tuned to one frequency range and the second tuned to another. Fine-tuning can be performed by employing a series of tuning vanes (for example, one per resonator probe). This allows a multiple frequency band system, where each frequency range can be fine-tuned, and therefore built without the need for multiple high performance switching devices. Multiple switching devices would significantly add to the resistive losses in the resonator and would negatively impact the system's Q factor and therefore its ultimate performance.

Additionally, the nature of the resonator probe 200 (strong magnetic fields generated on the inside and magnetic fields canceling on the outside), allows electromagnetic shielding to be placed in close proximity to the resonator probe 200 without disrupting the magnetic fields generated inside the resonator probe. Furthermore, the design of resonator probe 200 is such that it is less susceptible to electromagnetic interference, both generated and induced, thereby decreasing the need for electromagnetic shielding as compared to other probe designs. The overall system performance is equal or better when compared with other resonator probe designs. The NQR scanning system of the present invention is therefore more compact and less space consuming.

Figure 6:
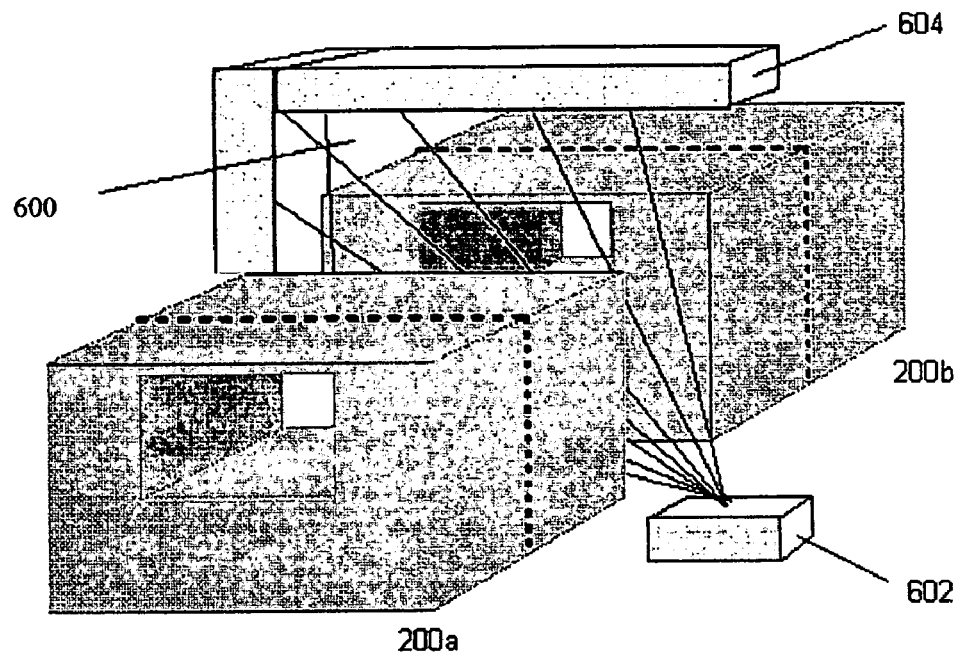
FIG. 6 is a diagram showing a baggage scanner configured to comprise two novel resonator probes and a transmission X-ray system.

One of the key features of the present invention is that not only can multiple resonator probes be integrated into a proximate and close-fitting electromagnetic shield but other types of equipment, including but not limited to CT Scanners and X-ray Scanners, can be closely integrated to produce a multi-technology system. FIG. 6 depicts and example of this integrated multi-technology system. A line-scan X-ray system 600, comprising X-ray generator 602 and a folded array of L-shaped X-ray detectors 604 is integrated with the dual coil NQR baggage scanner. Unlike conventional X-ray baggage scanners, NQR based baggage scanners only detect the presence of contraband in baggage without revealing their exact location in the baggage. Thus by integrating X-ray system 600 with the NQR based scanner, the scanning system will also be able to locate the contraband in the baggage.

A line-scan X-ray system 600 is provided in between the two resonator probes 200a and 200b. The fan shaped X-ray beams generated from X-ray generator 602 scans the luggage passing through inspection volume 104 on conveyor belt 340 and hits the X-ray detector 604. The system is equipped with an alarm circuit, which will activate upon suspicion.

Figure 7:
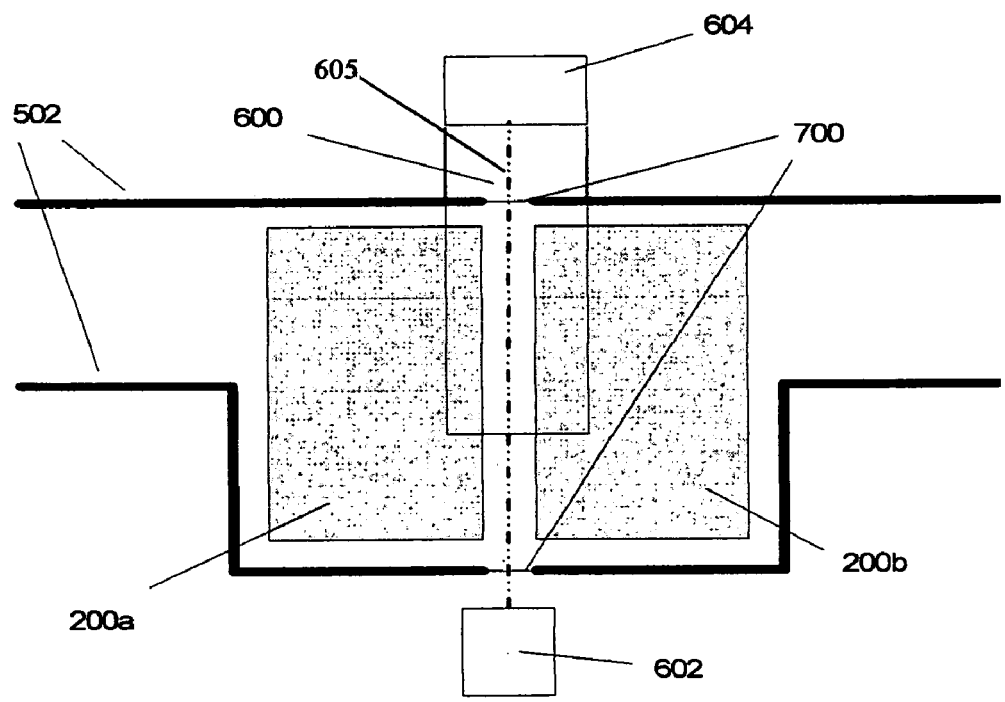
FIGS. 7 and 8 depict one embodiment of shielding for probes that have a thinned section of conductive material.
Figure 8:
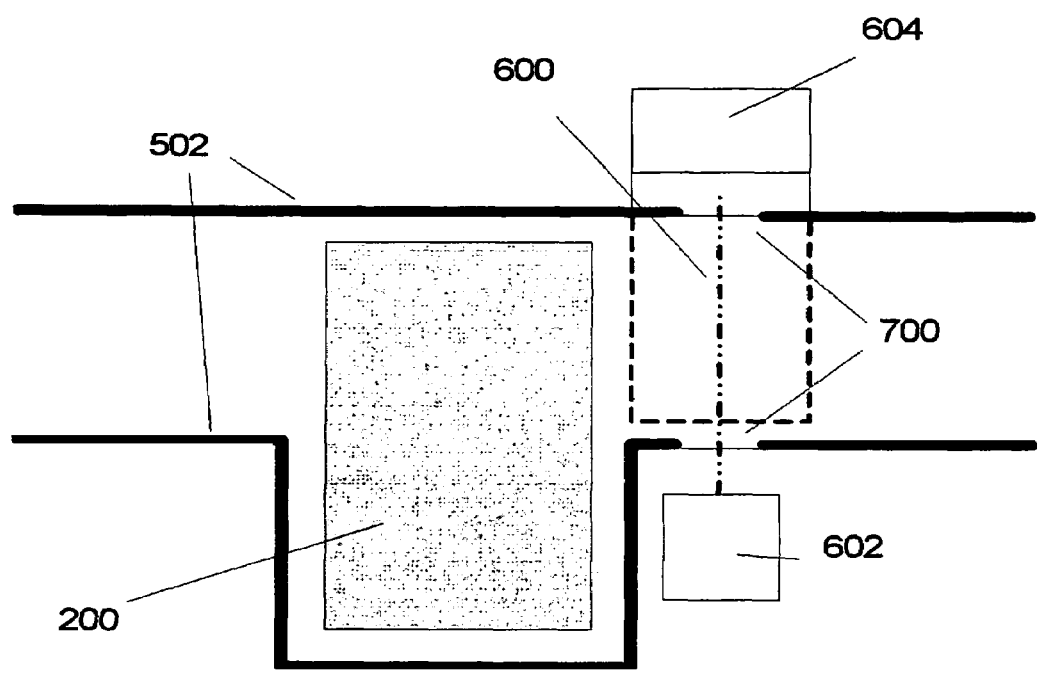

To allow CT scanners and/or X-ray scanners to be closely integrated to a produce a multi-technology system, it may be necessary to keep the X-ray or CT equipment outside of the electromagnetic shield used in conjunction with the resonator probe(s). Referring to FIG. 7, resonator probes 200a and 200b are surrounded by an electromagnetic shield 502. The X-ray scanner 600, having detectors 604 and a X-ray source 602, emits X-ray radiation. In order for the X-rays 605 used by the CT or X-ray scanner 600 to be allowed to pass through the electromagnetic shielding 502 relatively unattenuated, it is preferred that the shielding 700 through which the X-rays 605 are expected to pass is made of high conductivity material that is sufficiently thin and/or of a low density. The portion of electromagnetic shielding 700 which offers low attenuation to X-rays could be integral to the rest of the shield or be an insert or inserts of thinner high conductivity shielding material such as aluminum which would minimally interrupt the x-ray beam 605 between X-ray source 602 and X-ray detectors 604. In an alternative embodiment, shown in FIG. 8, a single probe 200 is encompassed by an electromagnetic shield 502 and, adjacent to the probe 200, a plurality of X-ray detectors 604 is positioned to receive X-rays from an X-ray source 602 where the X-rays pass through thinned or altered shielding 700 to minimize attenuation.

The inventions and embodiments thereof described here deal with a resonator probe design and its implementation, allowing for detection and analysis systems to be built at lower cost, with better quality in terms of system performance, and the ability to integrate with other sensing technologies more efficiently and more compactly. Although these resonator probe designs lend themselves well to conveyor belt systems, they can also be used for gravity fed systems, drive through vehicle screening systems, tote screening systems, and cart screening systems. The probe in accordance with the present invention can also be used in pharmaceutical and chemical production quality control, chemical analysis, strain gauge measurement, and pharmaceutical processing.

Although two specific embodiments are described above, various different apparatuses and systems can be employed without departing from the scope of invention. While embodiments of the invention has been described in detail, various modifications and other embodiments thereof can be devised by one skilled in the art without departing from the spirit and scope of the invention, as defined in the accompanying claims.

What is claimed is:

1. A resonator probe suitable for use in a magnetic resonance based material detection system, the resonator probe comprising:
   a hollow resonator probe body made from an electrically conductive material wherein the probe body has a rectangular volume and at least one resonant frequency;
   an inspection volume integrally formed within said hollow resonator probe body, said inspection volume defined by a platform base, an inner top wall, and two inner side walls, said inner side walls connecting the top inner wall and platform base, wherein a sample of material passes through the inspection volume; and
   capacitance means electrically connected to said hollow resonator probe body.

2. The resonator probe of claim 1, wherein said resonator probe body is an elongated, square sided toroid.

3. The resonator probe of claim 1, wherein said capacitance means is provided in said resonator probe body.

4. The resonator probe of claim 3, wherein said capacitance means is distributed around a split in the body.

5. The resonator probe of claim 3 wherein said capacitance means runs parallel to a magnetic flux path generated within said resonator probe body.

6. The resonator probe of claim 1, wherein said rectangular volume is an inductive portion of a resonant circuit.

7. The resonator probe of claim 1, wherein the resonant frequency of the resonator probe is determined by an inductance of the resonator probe and a capacitance of the capacitance means.

8. The resonator probe of claim 1, wherein the capacitance means is adjustable.

9. The resonator probe of claim 8, whereby said adjustable capacitance means allows the resonant frequency of the resonator probe to be adjusted.

10. The resonator probe of claim 7, wherein the inductance of the resonator probe is adjustable by providing a means to adjust a cross-sectional area of said resonator probe body.

11. The resonator probe of claim 10, wherein the means to adjust the cross-sectional area of the probe body is comprised of a tuning vane.

12. The resonator probe of claim 1, further comprising an outer electrically conductive electromagnetic shielding layer surrounding the resonator probe body having an opening aligned with said inspection volume.

13. The resonator probe of claim 12 wherein the outer electrically conductive electromagnetic shielding layer comprises thinned areas of conductive material which maintains shielding while permitting X-ray radiation to pass with minimal attenuation.

14. A magnetic resonance based material detection and/or analysis system comprising:
   a plurality of resonator probe bodies, wherein said plurality of resonator probe bodies comprise a hollow resonator probe body made from an electrically conductive material wherein the probe body has a rectangular volume and at least one resonant frequency, an inspection volume integrally formed within said hollow resonator probe body, said inspection volume defined by a platform base, an inner top wall, and two inner side walls, said inner side walls connecting the top inner wall and platform base, wherein a sample of material passes through the inspection volume, and capacitance means electrically connected to said hollow resonator probe body.
   radio frequency pulse generator connected to said probe for producing an applied magnetic field within at least one probe body;
   sensor for detecting a magnetic field produced by a sample after being exposed to said applied magnetic field; and
   a controller to selectively energize the radio frequency pulse generator and/or sensor.

15. The system of claim 14, further comprising: an inductance adjuster capable of varying the inductance of at least one resonator probe and a controller to control said inductance adjuster.

16. The system of claim 14 further comprising a conveyor for carrying objects through the inspection volume and a controller to control the conveyor.

17. The system of claim 14 further comprising at least one other detection and/or analysis system.

18. The system of claim 17 wherein said other detection and/or analysis system is one of the following: a CT scan system or a X-ray scan system.

19. A method of performing magnetic resonance based material detection and/or analysis comprising the steps of:
activating a radio frequency pulse generator to produce an applied magnetic field within at least one probe body; and
sensing a magnetic field produced by a sample after being exposed to said applied magnetic field; wherein the at least one probe body is hollow and made from an electrically conductive material; wherein the probe body has a rectangular volume; wherein an inspection volume is integrally formed within said hollow resonator probe body;
and wherein a capacitance means is electrically connected to said hollow resonator probe body.

* * * * *